US005759182A

United States Patent [19]

Varney et al.

[11] Patent Number: 5,759,182

[45] Date of Patent: Jun. 2, 1998

[54] CRYOSURGICAL PROBE WITH PRE-COOLING FEATURE

[75] Inventors: Kelvin John Varney, Andover; Simon Richard Reeves, Southhampton, both of United Kingdom

[73] Assignee: Spembly Medical Limited, United Kingdom

[21] Appl. No.: 637,819

[22] PCT Filed: Nov. 9, 1994

[86] PCT No.: PCT/GB94/02459

§ 371 Date: Nov. 1, 1996

§ 102(e) Date: Nov. 1, 1996

[87] PCT Pub. No.: WO95/13025

PCT Pub. Date: May 18, 1995

[51] Int. Cl.[6] .......... A61B 17/36

[52] U.S. Cl. .......... 606/21; 607/96; 607/104; 607/107; 606/23

[58] Field of Search .......... 606/20–23, 26; 607/96, 104, 105, 107, 113

[56] References Cited

U.S. PATENT DOCUMENTS

| | | | |
|---|---|---|---|
| 3,630,203 | 12/1971 | Sellinger . | |
| 5,108,390 | 4/1992 | Potocky et al. | 606/21 |
| 5,254,116 | 10/1993 | Baust et al. | 606/21 |
| 5,275,595 | 1/1994 | Dobak, III | 606/23 |
| 5,281,213 | 1/1994 | Milder et al. | 606/20 |
| 5,328,467 | 7/1994 | Edwards et al. | 607/122 |
| 5,403,309 | 4/1995 | Coleman et al. | 606/20 |
| 5,522,870 | 6/1996 | Ben-Zion | 607/104 |

FOREIGN PATENT DOCUMENTS

| | | | |
|---|---|---|---|
| 0173599 | 3/1986 | European Pat. Off. | F25B 9/02 |
| 2026324 | 2/1980 | United Kingdom | A61B 17/36 |
| 2226497 | 7/1990 | United Kingdom | A61B 17/36 |

*Primary Examiner*—William E. Kamm
*Assistant Examiner*—Carl H. Layno
*Attorney, Agent, or Firm*—Renner, Otto, Boisselle & Sklar, P.L.L.

[57] ABSTRACT

A cryosurgical probe comprises a probe head operable to be cooled by the expansion of a refrigerant gas within the probe head; a probe handle having means for precooling the refrigerant gas; and a flexible catheter linking the probe handle and the probe head, the catheter defining a channel for carrying precooled refrigerant gas from the probe handle to the probe head.

25 Claims, 4 Drawing Sheets

50
40
10
30
20

2/4

CRYOSURGICAL PROBE WITH PRE-COOLING FEATURE

BACKGROUND OF THE INVENTION

This invention relates to cryosurgical probes.

Cryosurgical probes employing a cooling element disposed at a distal end of a flexible catheter are used in the treatment of internal bodily organs such as the heart.

An example of a cryosurgical probe is disclosed in the British published patent application number GB-A-2 226 497. This probe comprises a handle portion. a flexible catheter and a probe head. The probe head may be cooled by the expansion of a refrigerant fluid within a cavity of the probe head.

In use, the probe head and catheter are inserted into, for example, a patient's blood vessel such as the femoral vein. and art steered so that the probe head occupies a position within the heart. High pressure refrigerant gas is then supplied through the catheter to the probe head to cause cryosurgical necrosis of small areas of the cardiac tissue which are responsible for malfunctions such as cardiac arrhythmias.

In contrast to, for example, rigid cryosurgical probes such as the probes described in GB-B-1457981 and GB-B-1108905, there are very severe constraints on the size of the probe head and the flexible catheter linking the probe head to the handle. These constraints tend to limit the maximum refrigerant flow to the probe head, and so the cooling efficiency of the probe head is particularly important.

The cooling efficiency of the probe head in this type of device is dependent on a number of factors, including the initial temperature of the high pressure refrigerant gas. For this reason, the probe head in GE-A-2 226 497 employs a heat exchanger comprising a spirally wound section of a gas delivery tube, to allow the exhaust (expanded) gas to cool the high pressure refrigerant. However, due to the size limitations of the probe head, this arrangement provides inefficient cooling of the refrigerant gas. The arrangement also leads to an undesirably bulky probe head. The size of the probe head limits the minimum vein diameter in which the probe can be used.

SUMMARY OF THE INVENTION

It is an aim of this invention to improve the cooling efficiency of a cryosurgical probe using a flexible catheter.

This invention provides a cryosurgical probe comprising: a probe head operable to be cooled by the expansion of a refrigerant fluid within the probe head; a probe handle having means for precooling the refrigerant fluid; and a flexible catheter linking the probe handle and the probe head, the catheter defining a channel for carrying precooled refrigerant fluid from the probe handle to the probe head.

The invention addresses the above problems by providing precooling of the refrigerant fluid (e.g. a gas) at the probe handle, rather than at the probe head. This allows a much more powerful precooling arrangement (e.g. a dedicated refrigeration apparatus rather than merely a heat exchanger for heat transfer with the exhaust gases) to be used, since the limits on the size of the probe handle are much less stringent than those relating to the probe head. The probe head and the flexible catheter can be made smaller, because there is no need to employ a heat exchanger at the probe head and because the increased efficiency of the probe head (using the pre-cooled refrigerant fluid) means that a lower fluid flow is required to the probe head. This allows the probe to be used in narrower veins or in younger patients. Also, a heat insulating and flexible material (such as a plastics material) can be used (in place of commonly used stainless steel) to transport the high pressure refrigerant in the catheter and probe head, since heat exchange at these points is no longer required.

In other words, this invention provides a cryosurgical catheter using a two-stage cooling process. The incoming refrigerant fluid is first pre-cooled by a relatively bulky but high-capacity refrigeration apparatus in the probe handle. This in turn makes the second stage of cooling, namely the expansion of the fluid in the probe head, more efficient.

Although various different precooling arrangements could be used, such as passing the refrigerant fluid through a heat exchanger surrounded by a cryogenic liquid such as liquid nitrogen, in an elegantly simple embodiment the same supply of refrigerant fluid is used (in different portions) for the precooling and for the probe head cooling. To this end, it is preferred that the probe handle comprises a conduit for carrying the refrigerant fluid to the flexible catheter, the conduit having an aperture such that a portion of the refrigerant fluid is allowed to expand within the probe handle.

Preferably the portion of the refrigerant fluid expands into an expansion chamber within the probe handle, the expansion chamber having an exhaust outlet communicating with an atmospheric air vent. This means that the fluid which passes to the probe tip is that portion which has not expanded within the handle.

In order to provide efficient heat exchange between the expanded fluid in the probe handle and the refrigerant fluid, it is preferred that the probe handle comprises means for directing refrigerant fluid. which has expanded through the aperture, along the outside of at least a part of the conduit, thereby allowing heat exchange between the expanded gas and the refrigerant fluid within the conduit.

Preferably the means for directing comprises a helical vaned structure for directing the expanded fluid in a helical path along at least a part of the conduit.

In a preferred embodiment the means for directing are operable to direct the expanded fluid in an opposite direction to the flow of refrigerant fluid through the conduit. This provides for convenient exhaust of the expanded fluid (away from the catheter) and also ensures that the temperature gradients of both the incoming refrigerant and the fluid expanded within the handle are in the same direction (cooler towards the catheter end of the handle).

For efficient heat transfer it is preferred that the conduit is a metal tube.

In order to provide a return path for exhaust gas from the probe head, and to avoid direct contact between the patient and the channel for carrying high pressure refrigerant (for safety reasons), it is preferred that the flexible catheter comprises an outer channel for carrying exhaust gas from the probe head to the probe handle and an inner channel, within the outer channel, for carrying refrigerant fluid from the probe handle to the probe head.

Since heat exchange is not required within the catheter, but flexibility of the catheter is desirable, it is preferred that the inner channel comprises a plastics tube. Plastics tubes are cheaper to manufacture and less likely to block by kinking than the previously used steel tubes.

Preferably the plastics tube is a polyamide tube having a thermal conductivity of less than 1 Watt per metre—Kelvin (W/mK).

It is preferred that the plastics tube has a rigidity modulus (EI) of less than 20 Newtons per square metre ($N/m^2$).

In order that the temperature of the probe head can be monitored, it is preferred that the probe head comprises a temperature sensor for detecting the probe head temperature.

It is preferred that the probe comprises control means for controlling the flow of refrigerant fluid to the probe head in response to the probe head temperature. In this way a negative feedback arrangement can be used to control the probe head temperature to be substantially a desired value.

Preferably the control means is selectively operable, under user control:

(i) to prevent and vent the flow of refrigerant fluid to the probe head;

(ii) to control the flow of refrigerant fluid to the probe head to control the probe head temperature to be substantially 0° Celsius; and (iii) to control the flow of refrigerant fluid to the probe head to control the probe head temperature to be cooled to a temperature below 0° Celsius, suitable for cryosurgical necrosis of a patient's tissue.

This arrangement allows a surgeon to cool a particular part of the patient's tissue to 0° Celsius, to cause the probe head to freeze to that tissue and to disable electrical activity within that tissue. If a malfunction such as a cardiac arrythmia ceases, the surgeon can then cause that tissue to be necrosed.

Preferably the control means comprises: means for detecting a sudden increase in the probe head temperature (warming); and means, responsive to a detection of a sudden increase in the probe head temperature, for preventing and venting the flow of refrigerant fluid to the probe head. Since a sudden increase in temperature (e.g. an increase to at least a predetermined temperature) can indicate an increase in the fluid back pressure (e.g. caused by a blockage), it is safer to shut off and vent the fluid flow in these circumstances.

In order to assist a surgeon in correctly positioning the probe head on a required portion of tissue, it is preferred that the probe head comprises one or more electrodes for detecting electrical impulses generated by a patient's bodily tissue. Preferably means are provided for displaying a visual indication of the electrical impulses.

In order to provide a coaxial cable arrangement for conducting the electrical signals, it is preferred that the flexible catheter comprises a strengthening electrically conductive braid for connecting one of the one or more electrodes to the probe handle.

In order to assist in steering the probe head in the region of the target tissue, it is preferred that the probe head is disposed at an angle with respect to the flexible catheter. Alternatively, a more complex steering system may be used, in which the flexible catheter comprises one or more control wires for linking the probe head to the probe handle, the one or more control wires being connected to the probe head such that longitudinal movement of the one or more control wires causes the orientation of the probe head to change with respect to the flexible catheter; and the probe handle comprises orientation control means, connected to the one or more control wires, for allowing a user to move longitudinally the one or more control wires.

The orientation control means could comprise, for example, slide controls connected to the control wires and mounted on the probe handle. However, in an advantageously simple embodiment the orientation control means comprises at least one rotatable crank connected to the one or more control wires.

Viewed from a second aspect this invention provides a cryosurgical probe comprising: a probe head operable to be cooled by the expansion of a refrigerant fluid within the probe head; a flexible catheter linking the probe handle and the probe head, the catheter defining a channel for carrying the refrigerant fluid from the probe handle to the probe head; means for detecting a sudden increase in the probe head temperature; and means, responsive to a detection of a sudden increase in the probe head temperature, for preventing and venting the flow of refrigerant fluid to the probe head.

Viewed from a third aspect this invention provides a cryosurgical probe control unit for controlling a cryosurgical probe having a probe head operable to be cooled by the expansion of a refrigerant fluid within the probe head, the unit comprising: means for supplying a refrigerant fluid to the probe head; means for detecting a sudden increase in the probe head temperature; and means, responsive to a detection of a sudden increase in the probe head temperature, for preventing and venting the flow of refrigerant fluid to the probe head.

Viewed from a fourth aspect this invention provides a cryosurgical probe handle connectable via a flexible catheter to a probe head operable to be cooled by the expansion of a refrigerant fluid within the probe head, the handle comprising means for precooling the refrigerant fluid.

BRIEF DESCRIPTION OF THE DRAWINGS

The invention will now be described by way of example with reference to the accompanying drawings, throughout which like parts are referred to by like references, and in which.

DETAILED DESCRIPTION

Figure 1:
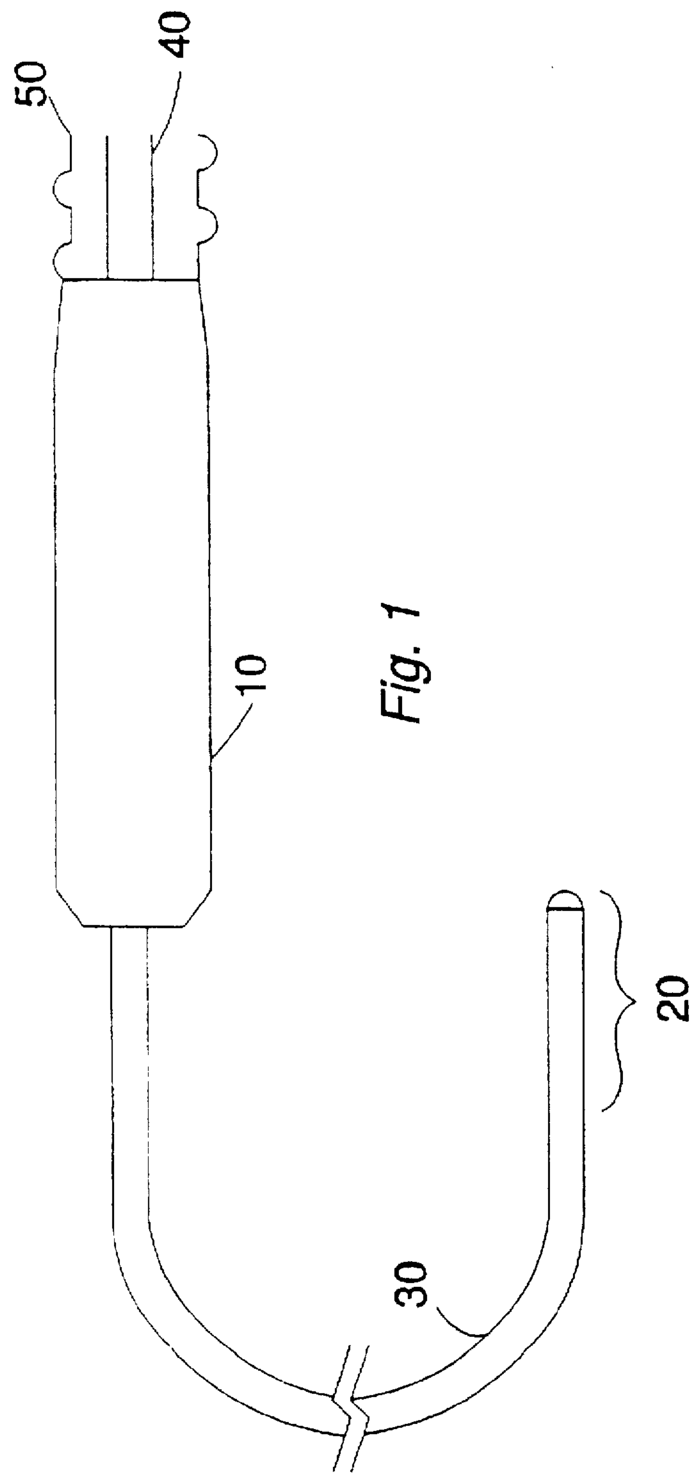
FIG. 1 is a schematic diagram of a cryosurgical probe.

Referring now to FIG. 1, a cryosurgical probe comprises a probe handle 10, a probe head 20, and a flexible catheter 30 linking the probe handle and the probe head.

The cryosurgical probe shown in FIG. 1 may be used in surgical procedures in which a patient's bodily tissue is locally cooled to such a degree that the tissue is locally destroyed. The cryosurgical probe has particular application to treatment of internal organs such as the human heart. In this case, the probe head 20 and the flexible catheter 30 are inserted into the femoral vein from a position in the patient's groin, and are passed through the patient's vein structure to reach the heart. Once the probe head 20 is in position in the patient's heart, the probe head can be cooled to destroy small portions of the hear tissue responsible for malfunctions of the heart such as arrhythmias.

The cooling of the probe head is performed using expansion of a refrigerant gas in accordance with the Joule-Thomson effect, described in the book 'Equilibrium Thermodynamics' (C J Adkins, Cambridge University Press, 1983). For this purpose, the refrigerant gas at a high pressure (e.g. $4\times10^6$ Pascals) is supplied to the probe handle 10 via an inlet tube 40, and exhaust (expanded) gas at a lower pressure is returned from the probe handle 10 by an exhaust tube 50.

The probe handle 10 comprises means for precooling the high pressure refrigerant gas to be used for cooling at the probe head. This precooling can improve the cooling performance of the probe head. The means for precooling will be described in detail below.

The flexible catheter 30 has a diameter of nominally 3 mm (conventionally referred to as a '9 French catheter'). The outer wall of the catheter 30 is strengthened with a metal braid, which is also used as an electrical conductor (see below).

Figure 2:
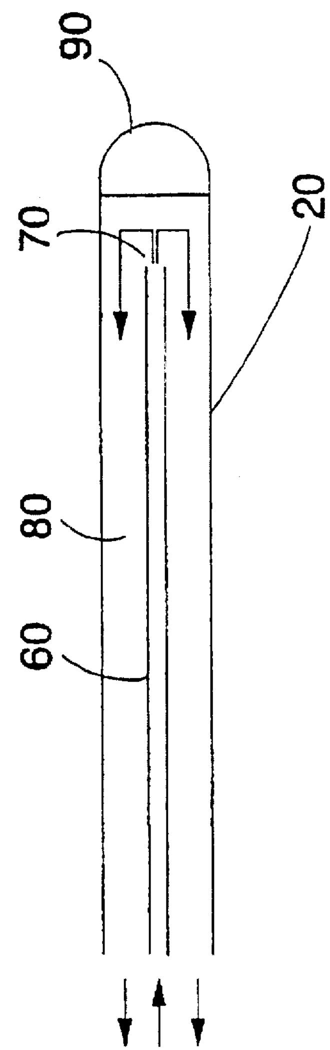
FIG. 2 is a schematic diagram illustrating the cooling operation of a probe head.

FIG. 2 is a schematic diagram illustrating the cooling operation of the probe head 20. In the probe head 20, high pressure refrigerant fluid is delivered through a narrow bore tube 60, and expands from the end 70 of the tube 60 into a larger exhaust cavity 80, this causes local cooling of a rounded metal tip 90 of the probe head by the Joule-Thomson effect.

The rounded metal tip 90 of the probe head 20 provides a smooth leading surface for the probe head 20 as it is directed along a patiert's blood vessels, and also allows effective heat conduction from the patient's tissue in contact with the tip 90 to the expanded refrigerant gas in the probe head 20.

Figure 3:
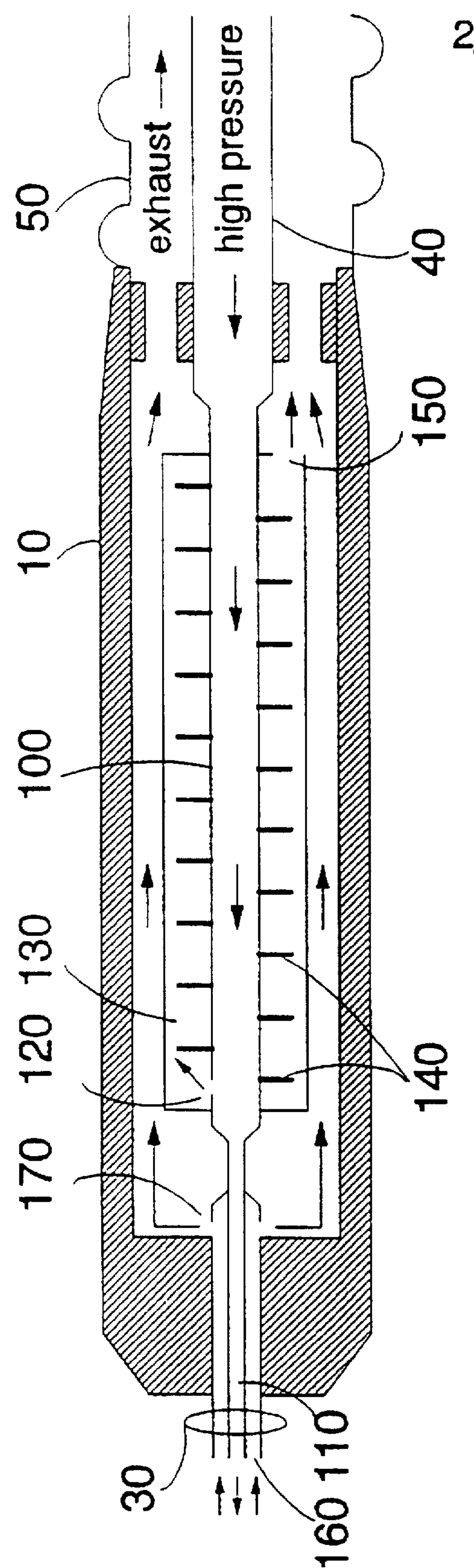
FIG. 3 is a schematic diagram illustrating the precooling operation of a probe handle.

FIG. 3 is a schematic diagram illustrating the precooling operation of the probe handle 10.

High pressure refrigerant gas received through the inlet tube 40 is passed through an axial conduit 100 in the probe handle 10 before entering an axial refrigerant supply tube 110 in the catheter 30 (connected to the tube 60 in the probe head 20).

The refrigerant supply is a polyamide tube having a thermal conductivity of less than 1 Watt per metre—Kelvin (W/mK) and a rigidity modulus (EI) of less than 20 Newtons per square metre ($N/m^2$).

An aperture 120 in the conduit 100 allows a portion (about two thirds) of the refrigerant gas to expand into an expansion area 130 of the probe handle 10. As mentioned above, this causes the expanded refrigerant gas to cool by the Joule-Thomson effect. The cooled gas is then directed by a helically-vaned heat exchanging structure 140 in a helical path around the conduit 100. This allows heat transfer from the high pressure refrigerant gas in the conduit 100 to the expanded gas in the expansion region 130, thereby precooling the high pressure refrigerant gas in the conduit 100. In order to assist the heat transfer, the conduit 100 and the vaned heat exchanger 140 are fabricated from a good heat conducting material such as copper.

A second aperture 150 allows the refrigerant gas which has expanded through the aperture 120 to escape along the exhaust tube 50.

The portion of the high pressure refrigerant gas which does not expand through the aperture 120 passes into the refrigerant supply tube 110 in the flexible catheter 30, to be supplied to the probe head 20. Exhaust gas from the probe head 20 returns to the probe handle through an exhaust return tube 160 which communicates with the exhaust cavity 80 in the probe head. This exhaust gas from the probe head 20 passes through apertures 170 into an outer region of the body of the probe handle 10, and from there into the exhaust tube 50.

Figure 4:
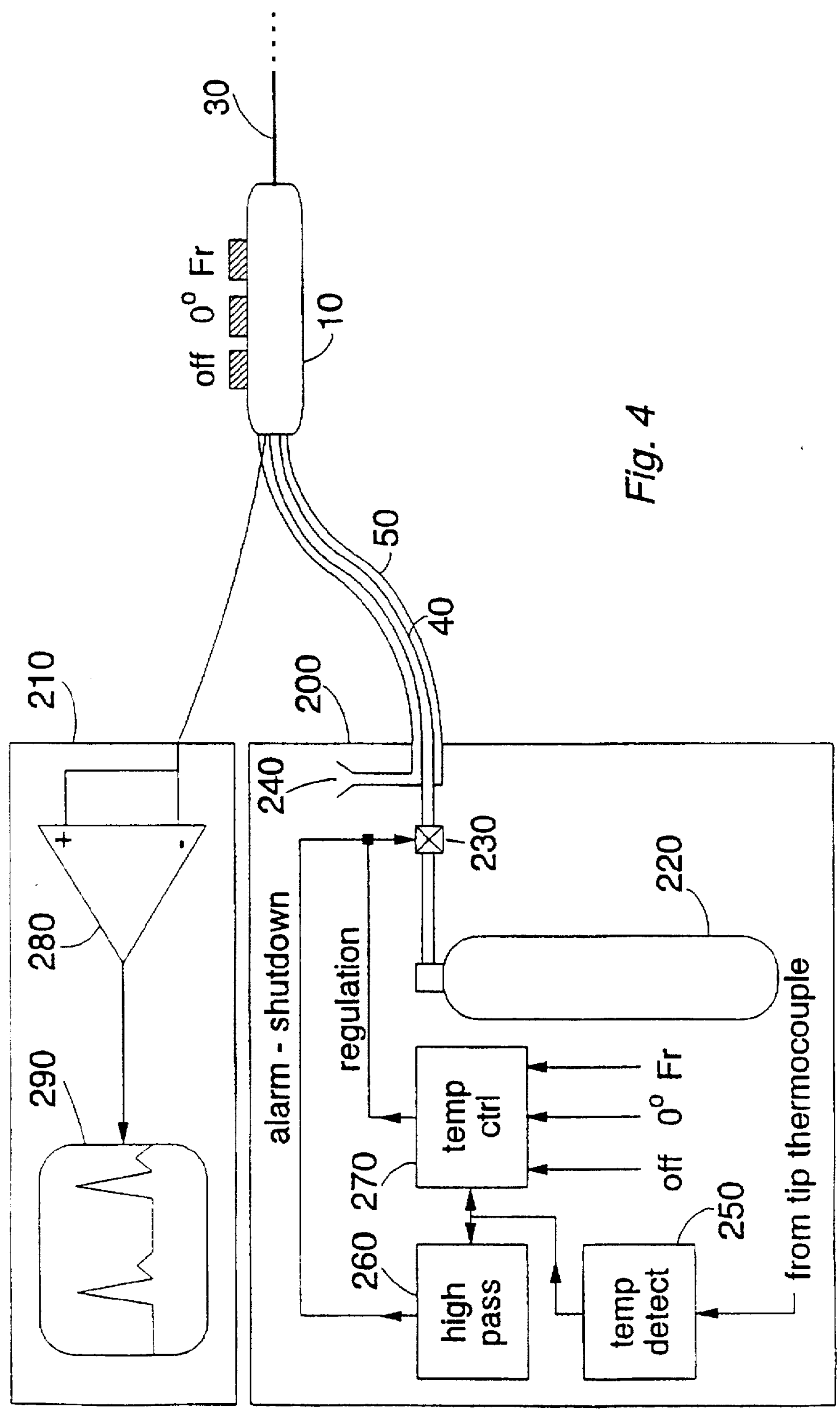
FIG. 4 is a schematic diagram illustrating a probe handle connected to a control apparatus.

FIG. 4 is a schematic diagram illustrating the probe handle 10 connected to control apparatus 200, 210.

The control apparatus 200 attends to the control of the flow of high pressure refrigerant gas to the probe handle 10 and, ultimately, to the probe head 20. The apparatus 200 comprises a vessel 220 containing high pressure refrigerant gas and connected, via a flow valve 230, to the inlet tube 40. The exhaust tube 50 from the probe handle is connected to an atmospheric air vent 240 or scavenging system.

A thermocouple temperature sensor is provided in the probe head 20. An electrical signal from the thermocouple sensor is passed, via signal wires (not shown) within the flexible catheter 30 and the exhaust tube 50 to a temperature detector 250 within the control apparatus 200. An output electrical signal from the temperature detector 250 is passed in parallel to a high pass electrical filter 260 and a feedback temperature controller 270.

The high pass filter 260 detects a sudden increase in the temperature of the probe head 20 (e.g. an increase over a threshold tip temperature such as −65° Celsius). Such a sudden increase indicates a corresponding increase in the back pressure (exhaust pressure) of the cooling operation in the probe head 20 and can therefore indicate a possible blockage in the exhaust return tube 160 or the exhaust tube 50. In this case, for safety reasons the flow of refrigerant gas to the probe handle 10 is immediately terminated by the high pass. filter 260 applying a control signal to the flow valve 230. The refrigerant supply tube 110 is also vented by an atmospheric air vent (not shown).

The feedback temperature controller 270 responds to either a variable temperature control (to be set by a surgeon or other operator using the cryosurgical probe) or, as shown in FIG. 4, to three possible temperature selections, namely 'Off', '0 Degrees' and 'Freeze'. In FIG. 4, these selections are made by control buttons mounted on the probe handle 10. However, in other embodiments, the temperature controls could be part of the control apparatus 200.

When the temperature control is set to 'Off', the flow of refrigerant gas to the probe handle 10 is shut off completely by means of a control signal from the feedback temperature controller 270 to the flow valve 230. The refrigerant supply tube 110 is also vented to an atmospheric air vent (not shown).

When the temperature control is set to '0 Degrees', the feedback temperature controller 270 varies the flow of refrigerant gas to the probe handle 10 using negative feedback in order to maintain a probe head temperature of substantially 0° Celsius.

When the temperature control is set to 'Freeze', the feedback temperature controller 270 controls the flow valve 230 to open fully, thereby decreasing the probe head temperature to a temperature (for example, −30° Celsius to −70° Celsius) suitable for cryosurgical necrosis of the patient's bodily tissue.

The reason for the three stage temperature control in this embodiment is as follows. During, for example, a surgical operation to eliminate cardiac arrythmia, it is necessary to destroy small parts of the heart tissue responsible for generating or transmitting spurious electrical signals within the heart which cause the arrythmia. However, it is important that incorrect parts of the heart tissue are not inadvertently destroyed.

In order to identify the correct portions of the tissue to be destroyed, the surgeon positions the probe head 20 at an approximately correct position within the heart, and then controls the probe head temperature to be reduced to substantially 0° Celsius. This has two effects: the metal tip 90 of the probe head 20 is frozen to a particular portion of the tissue, and electrical activity in that tissue is rendered inactive (although the tissue is not killed) by being cooled to the freezing point of water.

If the tissue to which the tip 90 is currently frozen is responsible for the cardiac arrythmia, then cooling that tissue to 0° Celsius will cause the arrythmia to be temporarily stopped. In this case, the surgeon can then operate the control to cause the probe head temperature to be reduced to a suitable temperature for cryosurgical necrosis of that area of tissue. The necrosis of the tissue is then performed without the probe head temperature rising above 0° Celsius, so that the tip 90 of the probe head 20 remains in contact with the same portion of tissue throughout the necrosis process.

If, however, cooling the probe head to 0° Celsius does not cause the arrythmia to cease, the surgeon knows that he had not yet identified the correct portion of cardiac tissue to be necrosed. In this case, the cooling of the probe head is stopped and, when the tip 90 has thawed and been freed from the tissue to which it was frozen, another area of cardiac tissue can be tested by cooling to 0° Celsius.

The control apparatus 210 in FIG. 4 comprises a signal amplifier 280 and a signal display 290. The signal amplifier 280 receives electrical impulses from electrodes disposed at the probe head 20 and amplifies those impulses for identification on the signal display 290. This provides a further aid to the surgeon to assist in correctly positioning the probe head 20 on the area of cardiac tissue to be destroyed.

Figure 5:
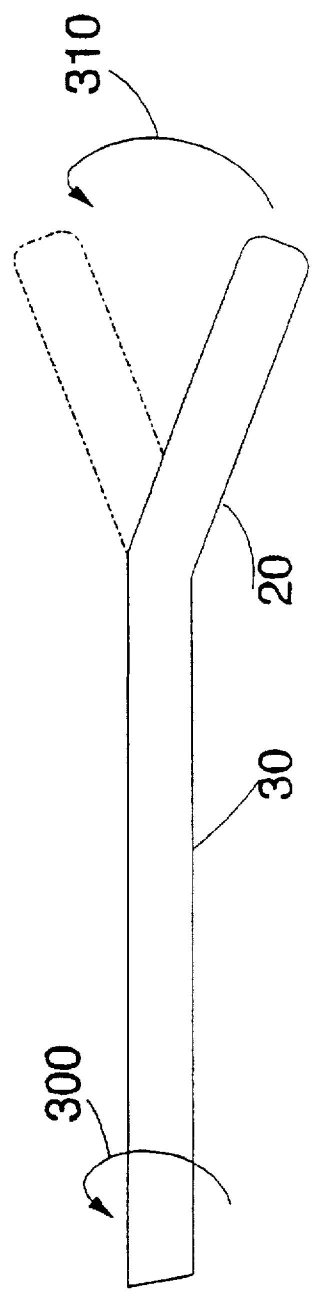
FIG. 5 is a schematic diagram illustrating steering of the probe head by torque control.

FIG. 5 is a schematic diagram illustrating steering of the probe head within the patient's blood vessels by torque control. In this embodiment, the probe head 20 is disposed at an angle to the flexible catheter 30. This means that axial rotation 300 of the flexible catheter 30 (for example by rotating the entire probe handle 10) causes a corresponding change 310 in the orientation of the probe head 20.

Figure 6:
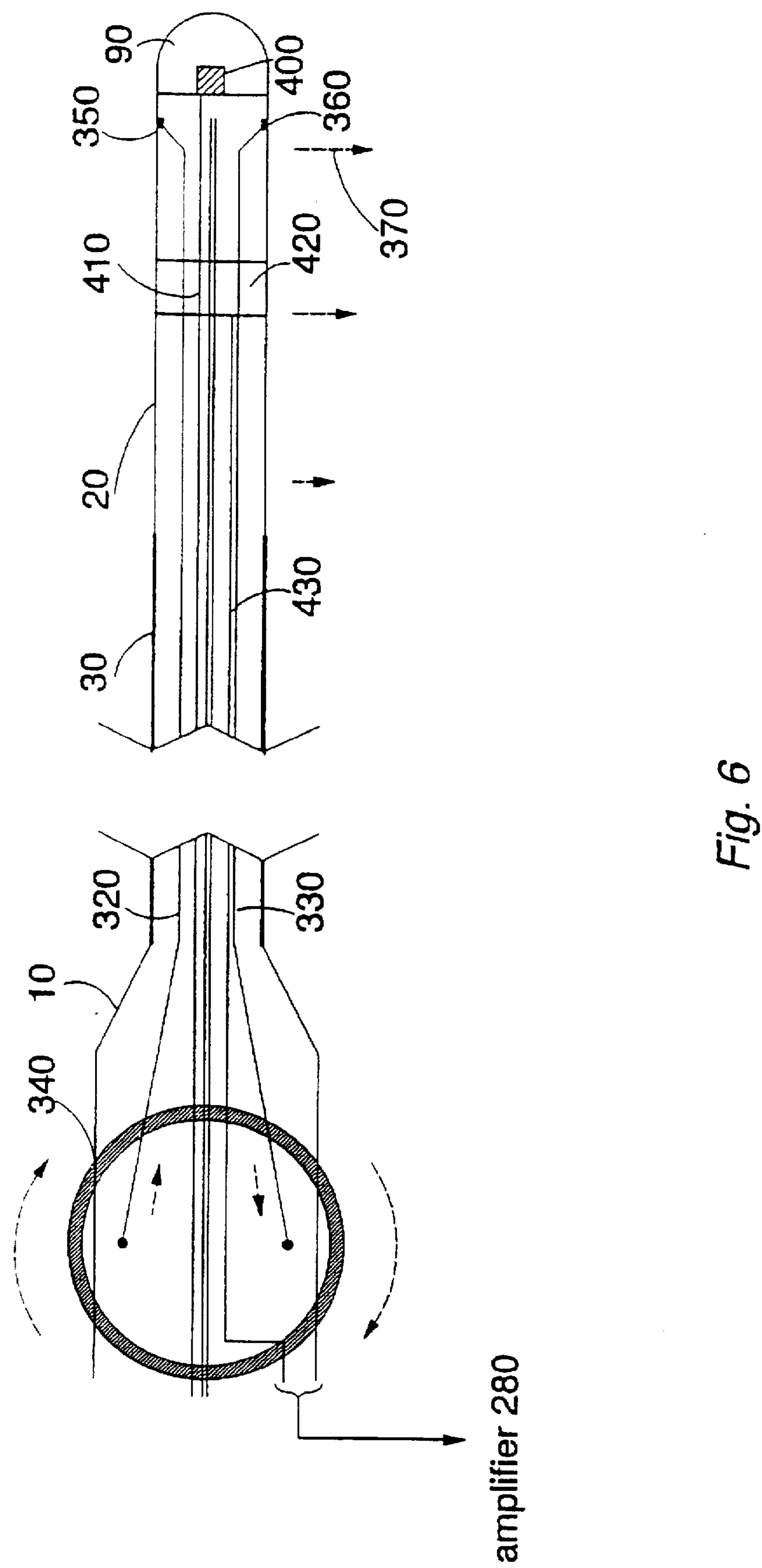
FIG. 6 is a schematic diagram of a two-axis steering mechanism.

FIG. 6 is a schematic diagram illustrating a two-axis steering mechanism for steering the probe head 20.

In FIG. 6, two control wires 320, 330 are connected to a rotatable crank 340 forming part of the probe handle 10. The control wires 320, 330 pass along the flexible catheter 30 into the probe head 20 and are linked to opposite sides 350, 360 of the probe head 20. This arrangement means that rotation of the crank 340 in, for example, a clockwise direction causes the control wire 320 to be pushed towards the probe head 20 and the control wire 330 to be pulled from the probe head 20. This in turn causes a downward movement 370 of the probe head 20.

This type of steering mechanism can be applied in two orthogonal directions, to provide a four-axis steering mechanism.

FIG. 6 also illustrates the thermocouple 400 connected via signal wires 410 to the temperature detector 250 in the control apparatus 200. Sensing of electrical impulses at the probe head is provided by two electrodes, one of which is the probe head tip 90 and the other which 420 is an annular metal ring around the probe head 20. The probe head tip 90 is connected to the probe handle 10 by a metal braid which is also used for strengthening the flexible catheter 30. The electrode 420 is connected to the probe handle 10 by a signal wire 430. This arrangement is similar to a coaxial cable and provides screening of the signal wire 430.

In another embodiment, four or more electrodes (for example three annular electrodes plus the probe head tip 90) could be used.

What is claimed is:

1. A cryosurgical catheter probe comprising:
   a probe head operable to be cooled by the expansion of a refrigerant gas within the probe head;
   a probe handle; and
   a flexible catheter linking the probe handle and the probe head, the catheter defining a channel for carrying refrigerant gas from the probe handle to the probe head;
   characterized in that the probe handle comprises a precooling device for precooling the refrigerant gas to be supplied via the catheter to the probe head.

2. A probe according to claim 1, in which the probe handle comprises a conduit for carrying the refrigerant gas to the flexible catheter, the conduit having an aperture such that a portion of the refrigerant gas is allowed to expand within the probe handle.

3. A probe according to claim 2, in which the portion of the refrigerant gas expands into an expansion chamber within the probe handle, the expansion chamber having an exhaust outlet communicating with an atmospheric air vent.

4. A probe according to claim 2, in which the probe handle comprises a director for directing refrigerant gas, which has expanded through the aperture, along the outside of at least part of the conduit, thereby allowing heat exchange between the expanded gas and the refrigerant gas within the conduit.

5. A probe according to claim 4, in which the director comprises a helical vaned structure for directing the expanded gas in a helical path along at least a part of the conduit.

6. A probe according to claim 4, in which the director is arranged relative to the conduit in an opposite direction, along the outside of the conduit, relative to the flow of refrigerant gas through the conduit.

7. A probe according to claim 2, in which the conduit comprises a metal tube.

8. A probe according to claim 1, in which the flexible catheter comprises an outer channel for carrying exhaust fluid from the probe head to the probe handle and an inner channel, within the outer channel, for carrying the refrigerant gas from the probe handle to the probe head.

9. A probe according to claim 8, in which the inner channel comprises a plastic tube.

10. A probe according to claim 9, in which the plastics tube is a polyamide tube having a thermal conductivity of less than 1 Watt per metre—degree Celsius (W/m°C) (1 Watt per metre—Kelvin (W/mK)).

11. A probe according to claim 9, in which the plastics tube has a rigidity modulus (EI) of less than 20 Newtons per square metre ($N/m^2$).

12. A probe according to claim 1, in which the probe head comprises a temperature sensor for detecting the probe head temperature.

13. A probe according to claim 1, in which the probe head comprises one or more electrodes for detecting electrical impulses generated by a patient's bodily tissue.

14. A probe according to claim 13, comprisig means for displaying a visual indication of the electrical impulses.

15. A probe according to claim 13 in which the flexible cath eter comprises a strengthening electrically conductive braid for connecting one of the one or more electrodes to the probe handle.

16. A probe according to claim 1, further comprising a means for connecting the probe head to the flexible catheter at an angle with respect to the flexible catheter.

17. A probe according to claim 1, in which:

the flexible catheter comprises one or more control wires for linking the probe head to the probe handle, the one or more control wires being connected to the probe head such that longitudinal movement of the one or more control wires causes the orientation of the probe head to change with respect to the flexible catheter; and a probe handle comprises orientation control mean, connected to the one or more control wires, for allowing a user to move longitudinally the one or more control wires.

18. A probe according to claim 17, in which the orientation control means comprises at least one rotatable crank connected to the one or more control wires.

19. A cryosurgical catheter probe system comprising:

a probe handle:

a probe head operable to be cooled by the expansion of a refrigerant fluid within the probe head;

a flexible catheter linking the probe handle and the probe head, the catheter defining a channel for carrying the refrigerant fluid from the probe handle to the probe head;

means for sensing the temperature of the probe head. and for providing an electrical signal indicative of the sensed temperature:

valve means operable by an electric control signal to prevent and vent the flow of refrigerant fluid to the probe head:

an electronic circuit coupled to the temperature sensor and to the valve means. for detecting a sudden increase in probe head temperature. and. in response thereto. controlling the valve means to prevent and vent the flow of refrigerant fluid to the probe head.

20. A probe system according to claim 19, in which the refrigerant fluid comprises a refrigerant gas.

21. A cryosurgical probe control unit for controlling a cryosurgical probe having a probe head operable to be cooled by the expansion of a refrigerant fluid within the probe head, the unit comprising:

means for supplying a refrigerant fluid to the probe head;

means for sensing the temperature of the probe head. and for providing an electrical signal indicative of the sensed temperature:

valve means operable by an electric control signal to prevent and vent the flow of refrigerant fluid to the probe head:

an electronic circuit coupled to the temperature sensor and to the valve means, for detecting a sudden increase in probe head temperature. and. in response thereto. controlling the valve means to prevent and vent the flow of refrigerant fluid to the probe head.

22. A catheter probe system comprising:

a probe head operable to be cooled by the expansion of a refrigerant gas within the probe head;

a probe handle; and a flexible catheter linking the probe handle and the probe head, the catheter defining a channel for carrying refrigerant gas from the probe handle to the probe head;

a precooling device in the probe handle for pre-cooling the refrigerant gas to be3 supplied via the catheter tot he probe head;

a temperature sensor in the probe head for detecting the probe head temperature; and control means for controlling the flow of refrigerant gas to the probe head in response to the probe head temperature.

23. A probe according to claim 22, in which the control means comprises:

means for detecting a sudden increase in the probe head temperature; and means, responsive to a detection ofa sudden increase in t he probe head temperature, for preventing and venting the flow of refrigerant fluid to the probe head and for venting exhaust fluid from the probe head.

24. A cryosurgical catheter probe according to claim 22, wherein the control means is arranged to be selectively operable, under user control;

(i) to prevent and vent the flow of refrigerant gas to the probe head;

(ii) to control the flow of refrigerant gas to the probe head to control the probe head tempreature to be substantially 0° C.; and (iii) to control the flow of refrigerant gas to the probe head to control the probe head temperature to be cooled to temperature below 0° C., suitable for cryosurgical necrosis of a patient's tissue.

25. A cryosurgical catheter probe handle comprising:

an inlet for receiving refrigerant gas;

a catheter connection region connectable to a flexible catheter to supply the refrigerant gas via the flexible catheter to a probe head operable to be cooled by the expansion of the refrigerant gas within the probe head;

a precooling device for pre-cooling the refrigerant gas within the probe handle to be supplied to the flexible catheter.

* * * * *